(12) United States Patent
Dooney, Jr. et al.

(10) Patent No.: US 10,085,739 B2
(45) Date of Patent: Oct. 2, 2018

(54) MEASURING TOOL USING SUTURE AND SUTURE ANCHOR

(71) Applicant: Arthrex, Inc., Naples, FL (US)

(72) Inventors: Thomas Dooney, Jr., Naples, FL (US); Alan M. Hirahara, Gold River, CA (US)

(73) Assignee: Arthrex, Inc., Naples, FL (US)

( * ) Notice: Subject to any disclaimer, the term of this patent is extended or adjusted under 35 U.S.C. 154(b) by 0 days.

(21) Appl. No.: 15/729,109

(22) Filed: Oct. 10, 2017

(65) Prior Publication Data

US 2018/0028173 A1 Feb. 1, 2018

Related U.S. Application Data

(62) Division of application No. 14/807,469, filed on Jul. 23, 2015, now Pat. No. 9,814,455.

(51) Int. Cl.
| | | |
|---|---|---|
| *A61B 17/58* | (2006.01) | |
| *A61B 17/60* | (2006.01) | |
| *A61F 2/00* | (2006.01) | |
| *A61B 17/04* | (2006.01) | |
| *A61B 90/00* | (2016.01) | |
| *A61F 2/08* | (2006.01) | |

(52) U.S. Cl.
CPC .......... *A61B 17/0401* (2013.01); *A61B 90/06* (2016.02); *A61B 2017/0412* (2013.01); *A61B 2017/0427* (2013.01); *A61B 2090/061* (2016.02); *A61F 2/08* (2013.01)

(58) Field of Classification Search
CPC combination set(s) only.
See application file for complete search history.

(56) References Cited

U.S. PATENT DOCUMENTS

| | | |
|---|---|---|
| 5,013,318 A | 5/1991 | Spranza, III |
| 6,427,351 B1 | 8/2002 | Matthews et al. |
| 7,134,216 B2 | 11/2006 | Rupp et al. |
| 7,329,272 B2 | 2/2008 | Burkhart et al. |
| 8,012,161 B2 | 9/2011 | Primavera et al. |
| 8,048,157 B2 | 11/2011 | Albertorio |
| 8,920,497 B2 | 12/2014 | Albertorio et al. |
| 9,005,246 B2 | 4/2015 | Burkhart et al. |
| 2008/0208204 A1* | 8/2008 | Schmieding ......... A61B 5/1072 606/102 |

* cited by examiner

*Primary Examiner* — Sameh Boles
(74) *Attorney, Agent, or Firm* — Blank Rome LLP

(57) ABSTRACT

Measuring tool, surgical constructs, and methods for measuring distances between two or more locations. A measuring device allows for simple and accurate intraoperative length measurements to be made. A measuring device has a distal end that can hold a flexible strand in a hole, eyelet, claw, or other suitable means. A shaft of the device has calibration markings on it, with the zero point at the end opposite the distal tip.

7 Claims, 3 Drawing Sheets

MEASURING TOOL USING SUTURE AND SUTURE ANCHOR

CROSS REFERENCE TO RELATED APPLICATION

This is a divisional of U.S. patent application Ser. No. 14/807,469, filed Jul. 23, 2015, the entire disclosure of which is incorporated herein by reference in its entirety.

BACKGROUND

The present disclosure relates to surgical devices tissue repairs and, in particular, to devices and measuring tools.

SUMMARY

Devices, tools, and methods for measuring distances between two or more point s or locations during surgical procedures are disclosed.

A measuring device allows for simple and accurate intraoperative length measurements to be made. A measuring device has a distal end that can hold a flexible strand in a hole, eyelet, claw, or other suitable means. A shaft of the device has calibration markings on it, with a zero point at an end opposite the distal tip.

A measuring device is provided with a flexible strand from a fixation device to span a distance either curved or straight, and determine accurate measurement. As the flexible strand is secured to the fixation device, it makes it a secure "zero" point to measure from.

A calibrated instrument holds a flexible strand (suture) at a distal tip of the instrument. A flexible strand is zeroed out with a marker or by a similar method. A calibrated instrument is then moved to a desired location and a flexible strand will slide along the instrument and the measurement can be determined. An arc length or curvature of a portion of a bone with a curvature may be determined.

DETAILED DESCRIPTION

Figure 1:
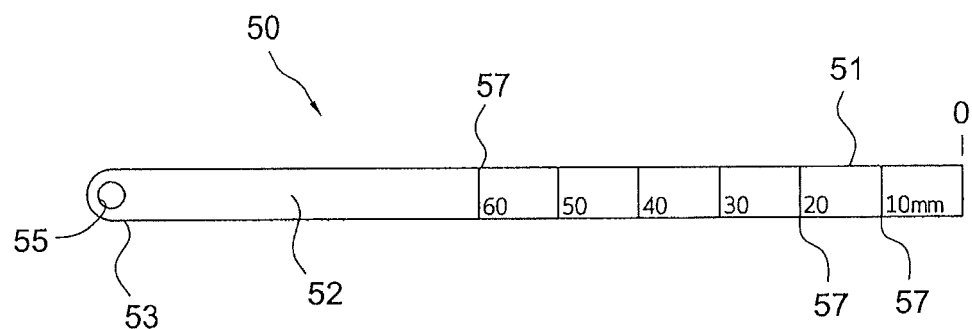
FIG. 1 illustrates a side view of a measuring tool according to an exemplary embodiment.

Surgical constructs, systems, measuring tools, and techniques for measuring distances between two or more locations during surgical procedures and soft tissue repair and fixation, such as fixation of soft tissue (ligament, tendon, graft, etc.) to bone are disclosed.

A measuring device allows for simple and accurate intraoperative length measurements to be made. A measuring device has a distal end that can hold a flexible strand in a hole, eyelet, claw, or other suitable means. A shaft of the device has calibration markings on it, with the zero point at the end opposite the distal tip.

A measuring device is provided with a flexible strand from a fixation device to span a distance either curved or straight, and determine accurate measurement. As the flexible strand is secured to the fixation device, it makes it a secure "zero" point to measure from.

A calibrated instrument holds a flexible strand (suture) at a distal tip of a shaft instrument. The flexible strand is zeroed out with a marker or by a similar method or with similar device. The calibrated instrument is then moved to a desired location on a bone surface, and the flexible strand will slide along the instrument and the measurement can be determined. A distance between two points, or an arc length or curvature of the bone surface of the portion of the bone spanned by the instrument may then be determined, for example, by reading graduated markings or calibrations on the shaft of the instrument, or by counting the number of graduated markings.

A measurement tool or arthroscopic measuring device may be utilized in an operation where an anchor with two suture ends extending therefrom has already been implanted. To make a measurement, a suture end is passed through the distal tip of the tool, and the distal tip is pushed down until it contacts the suture anchor. The suture end or ends are then marked in any suitable manner, or alternatively one suture end is rigidly clamped in place while the other suture end is passed through the instrument. The instrument is then moved to the desired location over a bone surface, and the suture end or ends will slide down the calibrations. The mark on the suture end will identify the distance traveled by the instrument. An arc length or curvature of the bone surface of the portion of the bone spanned by the instrument may then be determined, for example, by reading graduated markings or calibrations on the shaft of the instrument, or by counting the number of graduated markings.

A surgical construct includes a fixation device (a suture anchor) with a flexible strand (a suture) attached to the fixation device and connected to a calibrated instrument (measuring tool). The fixation device is inserted into bone at a first location. To make a measurement, one end of the flexible strand is passed through a closed eyelet at the distal tip of the calibrated instrument (measuring tool), and the distal tip is pushed down until the distal end of the calibrated instrument contacts the fixation device (suture anchor). The flexible strand is zeroed out with a marker or by a similar method or with similar device, i.e., the flexible strand is marked to indicate the zero point of the calibrated instrument. The calibrated instrument is then moved to a desired, second location on the bone surface. The flexible strand slides along the shaft of the calibrated instrument and the measurement/distance can be determined. A measured distance may indicate a location of a second fixation device (a second suture anchor). A second fixation device may secure tissue to bone, for example, soft tissue to bone. A second fixation device may also secure one or two ends of the flexible strand attached to the fixation device.

In an illustrative embodiment, a surgical construct comprises a fixation device with a body, a proximal end, a distal end, a longitudinal axis, and a flexible strand extending from the fixation device. A flexible strand may be securely attached to, and extend therefrom, the fixation device. In an embodiment, the flexible strand is passed through an opening at a most distal end of a calibrating instrument or device (measuring tool). A calibrating instrument is advanced over an outer surface of a substantially non-straight structure, for example, a bony curved structure, so that the flexible strand from the fixation device spans a distance either curved or straight, and determine accurate measurement. As the flexible strand is secured to the fixation device, it makes it a secure "zero" point to measure from.

Methods of length measurements and soft tissue repairs which allow precise placement and location of the tissue with respect to the bone are also disclosed. An exemplary method comprises inter alia: (i) inserting a fixation device (for example, an anchor) with an attached flexible strand (for example, suture or filament) into tissue at a first location; (ii) passing at least one limb of the flexible strand through an eyelet or opening of a calibrated shaft of a measuring instrument; (iii) moving the calibrated shaft with the flexible strand to a second location; and (iv) measuring a distance between first and second locations by determining a distance traveled by the at least one limb relative to the calibrated shaft. A second location may be indicative of placement of another fixation device. The another fixation device may secure the flexible strand. A second location may indicate an end of an arc or curvature of a portion of a bone with curvature such as, for example, glenoid, tuberosity, or condyle. The flexible strand may secure soft tissue to bone.

In another embodiment, a method of tissue repair comprises: (i) securing a surgical construct into bone, the surgical construct comprising a fixation device (for example, a suture anchor) and a flexible strand secured to the fixation device; (ii) passing first and second limbs of the flexible strand through a closed eyelet at a distal end of a calibrated measuring instrument; and (iii) using the first and second limbs to measure a distance between two locations over a surface of the bone. In an embodiment, the first and second limbs slide along a shaft of the instrument and the measurement can be determined by reading the calibrations or graduated markings on the shaft of the instrument. Distance x may indicate a distance between the fixation device and another fixation device. Distance x may indicate an arc length of a portion of the bone with a curvature.

Referring now to the drawings, where like elements are designated by like reference numerals, FIGS. 1-4 illustrate exemplary device 50 (measuring tool 50 or arthroscopic measuring device 50) of surgical construct 100 for intraoperatively measuring distance "x" between two operative locations, for example, between locations of two fixation devices secured into body tissue such as bone. Surgical construct 100 may also be employed to determine an arc length or curvature of a portion of a bone with a curvature, or to determine the comet placement of two or more fixation devices over a portion of bone with or without curvature.

Surgical construct 100 is formed of device 50 (measuring tool or measuring device 50) and fixation device 10 provided with flexible strand or flexible material 30 (suture 30) secured to (attached to) the fixation device 10. In an exemplary embodiment, the flexible strand 30 is a suture strand 30 and the fixation device 10 is a suture anchor 10. Flexible strand 30 operatively extends between the fixation device 10 and the device 50.

Device 50 (measuring tool or measuring device 50) includes a shaft 52 with a proximal end 51 and a distal end 53. A closed eyelet 55 (opening, hole, claws or similar structure 55) is provided at distal end 53. Closed eyelet 55 is sized to allow easy passage of one or more limbs of flexible strand 30 to pass therethrough and to aid in methods of assessing and determining a length or distance between two or more points/locations on a tissue surface (for example, an arc length of a surface of a portion of bone with a curvature). A plurality of graduated markings 57 (set of gradations 57) are provided on shaft 52 of the measuring tool or device 50, starting from the proximal end 51. In an exemplary embodiment, graduated markings 57 extend from a "zero" point to a "60 mm" point, as shown in FIG. 1, with zero point coinciding with a most proximal end of shaft 52.

In an exemplary embodiment, fixation device 10 is in the form of a suture anchor 10 (for example, a knotless suture anchor 10) having an anchor body 11 provided with a longitudinal axis 11a, a proximal end 13, and a distal end 12. A plurality of ribs, ridges, or threads 15 may extend circumferentially around at least a part of anchor body 11. A cannulation may be provided within anchor body 11 and extends along the body 11, to allow one or more flexible strands 30 to pass therethrough. Flexible strand 30 may be a suture strand or any suture-like material known in the art that could pass through or around tissue and could be further secured to another fixation device. Flexible strand 30 may be securely attached to fixation device 10 by known methods in the art such as insert molding, for example.

Anchor 10 may be a screw-in anchor or a push-in style anchor. Anchor 10 may be forming of metals, metal alloys, biocompatible plastics such as PEEK, or a bioabsorbable material such as PLLA material. A socket may be provided at the proximal end 13 of the anchor 10, to securely engage a tip of a driver. Anchor 10 may be made of one or more pieces, or may be provided as an integrated device.

Figure 2:
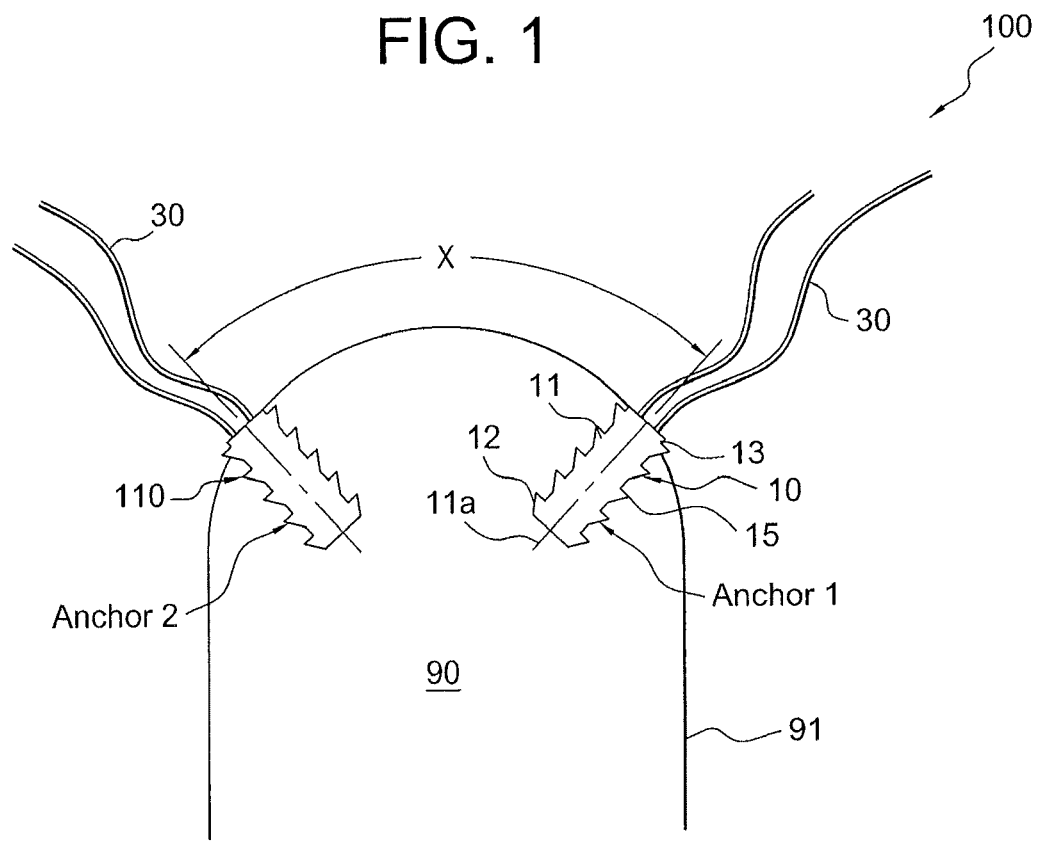
FIG. 2 illustrates a schematic view of a distance between two exemplary points (corresponding to two fixation devices) to be measured with the measuring tool of FIG. 1.

Reference is now made to FIG. 2 which illustrates a length or distance "x" between two fixation devices, for example, between first fixation device 10 and second fixation device 110, to be measured with device 50 of surgical construct 100. Second fixation device 110 may have been already provided within tissue (for example, bone 90) and thus distance "x" indicates the distance between the two inserted fixation devices 10, 110. Alternatively, distance "x" may indicate the correct placement/location of where the second fixation device 110 will be inserted/affixed to bone.

FIG. 2 depicts a first fixation device 10 (suture anchor 10) placed into bone 90 at a distance "x" away from a second fixation device 110 (a second anchor 110) that is needed, i.e., that needs to be secured to bone 90, or that has been already secured into bone. The instrument 50 uses the suture 30 from the first anchor 10 to measure distance "x". The instrument 50 can hold the suture 30 at the distal tip (with a hole 55 or claws) and has calibrations or graduated markings 57 on it.

A method of measuring a distance over straight or curved bone surfaces with device 50 of surgical construct 100 is detailed below with reference to FIGS. 3 and 4.

Figure 3:
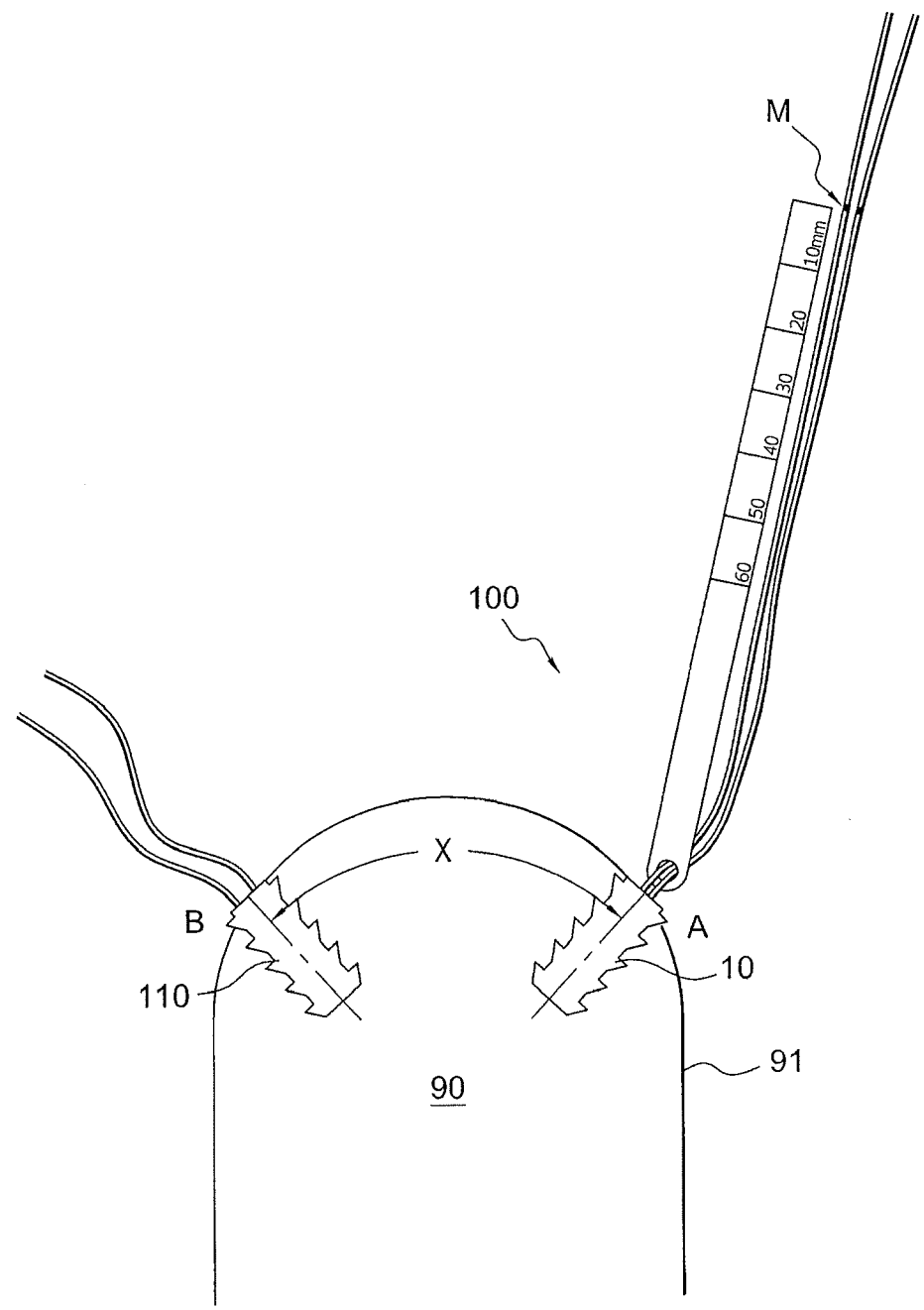
FIGS. 3 and 4 illustrate an exemplary method of intraoperative length measurement with the measuring tool of FIG. 1.

FIG. 3: fixation device 10 (suture anchor 10) is secured into bone 90 at a first location A on outer bone surface 91. The sutures 30 from the fixation device 10 (suture anchor 10) are fed through the opening 55 of the distal end 53 of device 50, and the distal end 53 is pushed down the sutures 30 until the distal end 53 of the instrument 50 contacts suture anchor 10. The sutures 30 are then marked M at the zero point of the instrument 50 (i.e., at a most proximal end of the instrument 50 which indicates 0 mm marking). Alternatively, one suture limb can be rigidly fixed with a clamp. The other single limb can be used through the instrument 50. Instead of marking with a marker, the sutures 30 could be held in a type of clamp at the zero point on the instrument and the clamp can slide down the shaft.

Figure 4:
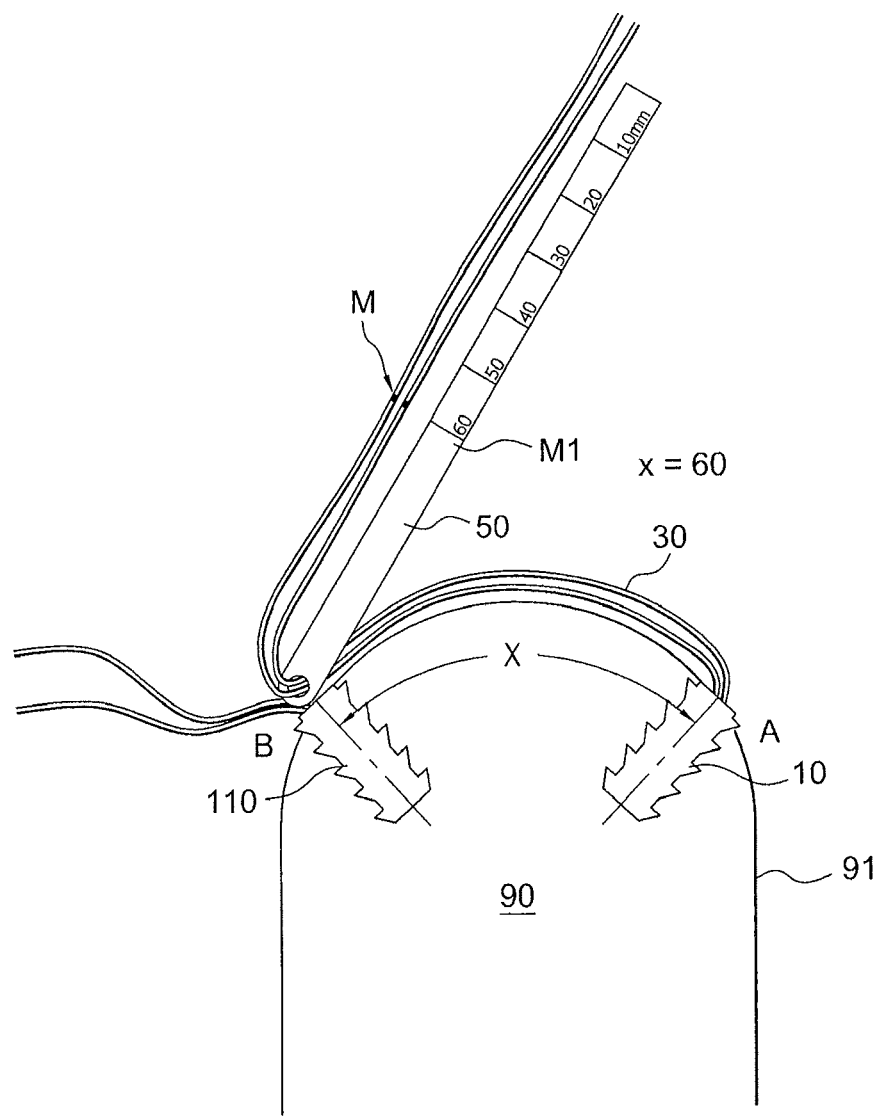

FIG. 4: The instrument 50 is then moved to the desired location, i.e., a second location B on outer surface 91 of bone 90. Sutures 30 will slide down the shaft 52 and calibrations 57 to position M1. The mark M on the suture will identify the distance "x" traveled by the instrument 50. In an exemplary embodiment, position M1 corresponds to markings 60 mm, thus distance x=60 mm.

The surgical constructs and systems detailed above are used in conjunction with any tissue repairs such as attachment of soft tissue to bone which require determining distances over straight or curved bone surfaces, and attach soft tissue to bone with various fixation devices such as screws, anchors, and implants, among many others.

A method of determining a distance between two different points or locations on a bone surface comprises: (i) securing a fixation device 10 (for example, a suture anchor 10) into bone 90, the fixation device 10 having at least a flexible strand 30 secured thereto; (ii) passing the flexible strand 30 through a closed opening 55 of a measuring tool 50; and (iii) using the flexible strand 30 from the fixation device 10 to measure a distance x between the fixation device 10 and another location B on the bone 90. In an embodiment, the measuring tool 50 is provided with a plurality of graduated markings or calibrations 57. By moving the instrument 50 from a first location A (coinciding with the location where the first fixation device 10 has been installed into bone 90) to second location B on the bone 90, the flexible strand 30 will slide down a shaft 52 of the measuring tool 50 and indicate the distance x traveled by the measuring tool 50.

An exemplary application of the measuring tool 50 is shoulder arthroscopy, which requires measuring of arcs over the glenoid or shoulder tuberosity. As the arcs are non-straight lines, measuring these distances is facilitated by the measuring instrument, surgical construct, and methods of the present disclosure, especially when a surgeon needs to come from non-right angles with variable angles of measurements.

Device 50 and surgical construct 100 detailed above use a suture/flexible strand attached to a fixation device as a guide over the arc or distance of the bone structure to be measured. The distance on the calibrated device 50 may be measured extra-articularly, so a surgeon will not need to read the markings/numbers inside (i.e., intra-articularly). The measurement is predictable and accurate as instrument 50 and surgical construct 100 provide a steady method with a fixed location (the suture secured into suture anchor, providing a "zero" point to measure from).

Fixation devices 10, 110 may be any of swivel and/or screw-in suture anchors and/or push-in suture anchors (such as an Arthrex SwiveLock® anchor, disclosed in U.S. Pat. No. 9,005,246 or a PushLock® anchor, as disclosed in U.S. Pat. No. 7,329,272). Fixation devices 10, 110 may be also any anchors, implants or screws (such as interference screws or tenodesis screws) or any fixation element that allows attachment/fixation of the limbs of flexible strand 30 to bone. The fixation devices/implants may have various sizes (various diameters and/or lengths) and may be formed of biocompatible materials such as PEEK, biocomposite materials, metals and/or metal alloys, or combination of such materials, among others. Flexible strand 30 may further be provided around or through tissue to attached to another tissue, for example, through or around soft tissue to be secured/attached to bone.

Flexible strand 30 may be a suture strand or any suture-like material known in the art that could pass through tissue and eyelet 55 of the measuring tool 50. May include a high-strength suture, such as an ultrahigh molecular weight polyethylene (UHMWPE) suture. High strength suture may be a FiberWire® suture (Arthrex). FiberWire® suture is formed of an advanced, high-strength fiber material, namely ultrahigh molecular weight polyethylene (UHMWPE), sold under the tradenames Spectra® (Honeywell International Inc., Colonial Heights, Va.) and Dyneema® (DSM N.V., Heerlen, the Netherlands), braided with at least one other fiber, natural or synthetic, to form lengths of suture material. Flexible strand 30 may be also formed of a stiff material, or combination of stiff and flexible materials, depending on the intended application. The strand may be also coated and/or provided in different colors.

What is claimed is:

1. A method of measuring distance between two or more locations on body tissue during surgery, comprising: securing a fixation device in the body tissue, the fixation device comprising a body and a flexible strand attached to the body; passing at least one limb of the flexible strand through a closed eyelet of a distal end of a measuring tool; using the at least one limb of the flexible strand from the fixation device to measure a distance between the fixation device and another location on the body tissue, with the measuring tool; advancing the distal end of the measuring tool down the at least one limb of the flexible strand, so that the distal end of the measuring tool contacts the fixation device; marking the at least one limb of the flexible strand at a most proximal end of the measuring tool; moving the measuring tool to the another location on the bone, so that the at least one limb of the flexible strand slides down the measuring tool; and determining a calibration or gradation on a shaft of the measuring tool that corresponds to the distance between the fixation device and the another location on the bone.

2. The method of claim 1, wherein the body tissue is bone.

3. The method of claim 1, wherein the body tissue is shoulder under arthroscopy, and the fixation device is a screw-in or a push-in anchor.

4. The method of claim 1, wherein the surgery is arthroscopic surgery.

5. The method of claim 1, wherein the flexible strand is suture and the fixation device is a knotless suture anchor.

6. The method of claim 1, further comprising securing the at least one limb of the flexible strand with additional fixation devices.

7. The method of claim 6, wherein the additional fixation devices are knotless anchors.

* * * * *